United States Patent [19]

Lewis, Jr. et al.

[11] 4,180,696

[45] Dec. 25, 1979

[54] CONVERTING REACTIVE IMPURITIES IN ISOBUTANE CHARGE STREAM WITH CATALYST PHASE IN SULFURIC ACID ALKYLATION

[75] Inventors: Charles T. Lewis, Jr., Houston; Gerald F. Prescott, Bridge City, both of Tex.

[73] Assignee: Texaco Inc., White Plains, N.Y.

[21] Appl. No.: 953,382

[22] Filed: Oct. 23, 1978

[51] Int. Cl.$^2$ ............................................. C07C 3/54
[52] U.S. Cl. .................................. 585/717; 585/719; 585/730
[58] Field of Search ................... 260/683.59, 683.62, 260/683.61

[56] References Cited

U.S. PATENT DOCUMENTS

| | | | |
|---|---|---|---|
| 2,281,248 | 4/1942 | Putney | 260/683.61 |
| 2,348,467 | 5/1944 | Goldsby et al. | 260/683.61 |
| 2,465,049 | 3/1949 | Wolk | 260/683.61 |
| 3,053,917 | 9/1962 | Bergougnou | 260/683.59 |
| 3,098,108 | 7/1963 | Preiser | 260/683.62 |
| 3,109,042 | 10/1963 | Mayer | 260/683.59 |
| 3,239,578 | 3/1966 | Samuelson | 260/683.62 |

*Primary Examiner*—George Crasanakis
*Attorney, Agent, or Firm*—Carl G. Ries; Robert A. Kulason

[57] ABSTRACT

An alkylation process wherein isoparaffin hydrocarbons are alkylated with olefin hydrocarbons in the presence of an alkylation catalyst comprising $H_2SO_4$ to yield alkylated hydrocarbons suitable for use in motor fuels. Such process includes an isoparaffin pretreatment step wherein isoparaffin charge is contacted with spent alkylation catalyst to remove contaminants from the isoparaffin which are reactive with sulfuric acid under alkylation conditions.

3 Claims, 1 Drawing Figure

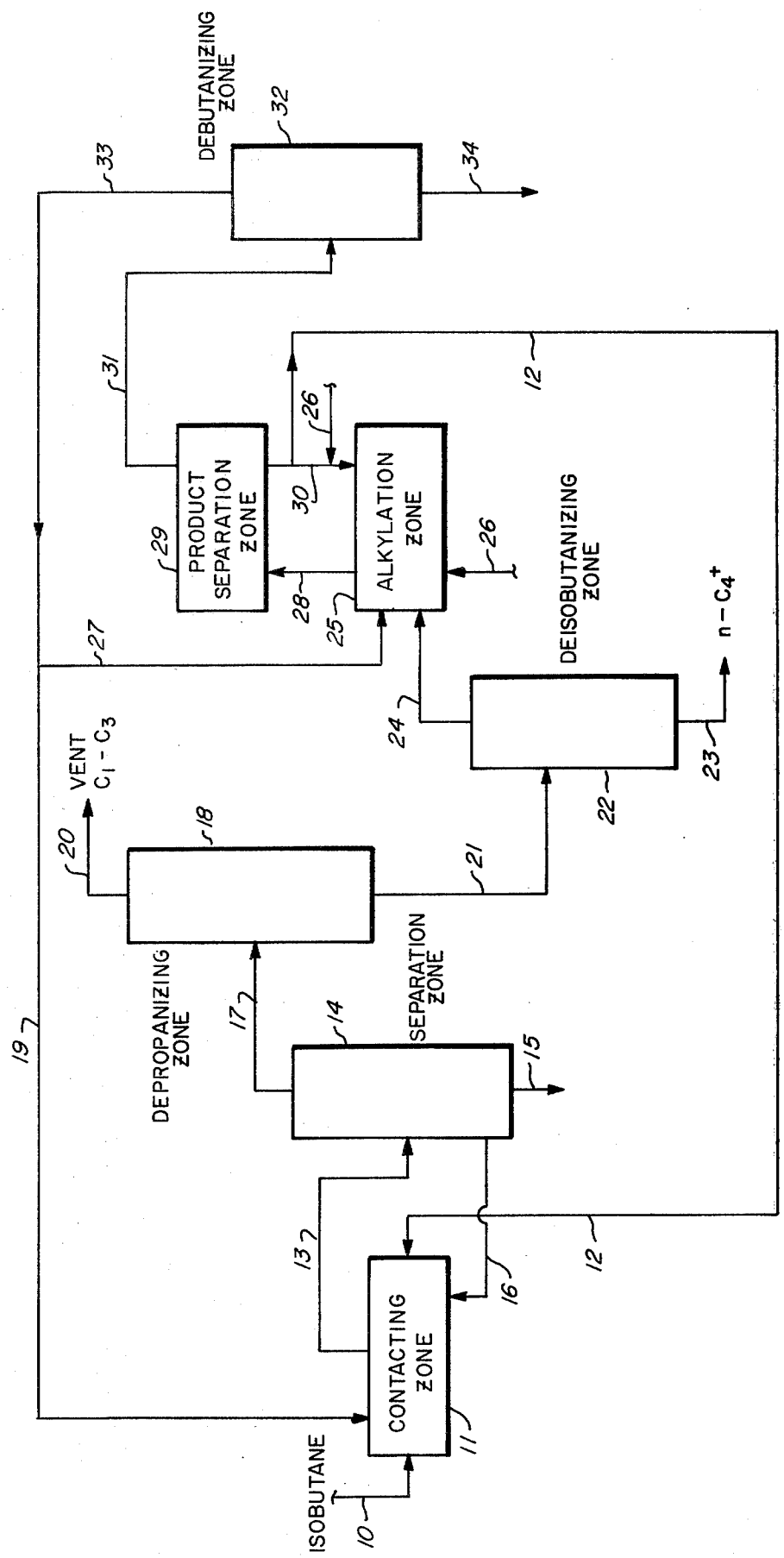

CONVERTING REACTIVE IMPURITIES IN ISOBUTANE CHARGE STREAM WITH CATALYST PHASE IN SULFURIC ACID ALKYLATION

BACKGROUND OF THE INVENTION

The present invention relates to alkylation of isoparaffins with olefins to produce branched chain paraffin hydrocarbons. More particularly, the present invention relates to the alkylation of isobutane with butylenes and propylene employing an alkylation catalyst comprising $H_2SO_4$. Specifically, the present invention relates to an improved method for removing impurities from an isobutane charge stream to such an alkylation process, which impurities are reactive with sulfuric acid under alkylation conditions. The improved method of the present invention comprises treating an isobutane charge stream with spent, $H_2SO_4$ containing alkylation catalyst to remove reactive impurities such as water, $H_2S$, mercaptans, etc. from the isobutane stream.

Alkylation of branched chain isoparaffin hydrocarbons with olefin hydrocarbons in the presence of an alkylation catalyst is well known. Processes for the alkylation of relatively low molecular weight isoparaffin hydrocarbons such as isobutane, isopentane, etc. with olefin hydrocarbons such as propylene and/or butylene to produce branched chain hydrocarbons suitable for use in motor fuel are widely practiced in commercial facilities.

Alkylation reactions of isobutane with butylene and/or propylene, and catalyzed by sulfuric acid containing catalyst, are carried out in the liquid phase under conditions such that a hydrocarbon phase comprising isobutane is maintained in intimate contact with a liquid catalyst phase comprising sulfuric acid. Alkylation reaction conditions include temperatures in the range of from about $-20°$ to $100°$ F., pressures of from about 45 to 400 psia, and residence times of reactants under alkylating conditions of from about 30 seconds to about 60 minutes. Isobutane to olefin molar ratios employed may be from about 2:1 to about 25:1 and volume ratios of hydrocarbon phase to catalyst phase of from about 0.5:1 to about 3:1 may be employed.

Olefin charge stocks to such alkylation processes may not be completely pure, and may contain such impurities as butane, propane, and ethane. Such normal paraffin hydrocarbons are unaffected by the alkylation reaction. In continuous alkylation processes employing hydrocarbon recycle streams (primarily unreacted isobutane), such normal paraffin hydrocarbons must be removed from the alkylation process. Propane and ethane are generally removed from alkylation processes by venting as a gas stream, whereas n-butane is commonly removed by fractional distillation. It is desirable that a relatively high conversion of olefin charge be obtained in the alkylation reaction by obtaining high olefin conversion on a one-pass basis. Consequently, the ratio of isobutane to olefin is generally maintained sufficient to obtain substantially complete olefin conversion.

Isobutane charge may contain hydrocarbon impurities such as propane and normal butane, which are not converted in the alkylation process (as well as water, mercaptans, hydrogen sulfide, etc.). As isobutane is commonly employed in substantial molar excess to olefin charge in an alkylation process, it is common practice to recycle an isobutane-containing stream to the alkylation reaction. The hydrocarbon impurities, such as propane and normal butane, if allowed to accumulate in the isobutane recycle stream, would soon reach a concentration sufficient to interfere with the alkylation reaction by diluting the isobutane concentration in the hydrocarbon phase. Therefore, in commercial processes, the isobutane for recycle is commonly fractionated to separate such impurities as propane and normal butane therefrom.

Sulfuric acid containing about 1–7 wt. percent water is an effective catalyst to promote alkylation of isobutane with olefins. Such sulfuric acid may be used alone, or in combination with other catalysts such as flurosulfonic acid, and/or with catalyst promoters and surfactants. Catalyst containing sulfuric acid is added to the alkylation process whereupon it contacts olefin and isoparaffin hydrocarbons in the reaction zone. Olefin, being slightly soluble, mixes with $H_2SO_4$ to form a liquid catalyst phase. Isobutane is substantially insoluble in such catalyst and forms a separate liquid phase. In the reaction zone, the two liquid phases are subjected to agitation to form an emulsion such that isoparaffin and olefin hydrocarbons are brought into intimate contact in the presence of the alkylation catalyst. Upon completion of the reaction step, the hydrocarbon phase (comprising alkylate and unreacted isobutane) and catalyst phase are separated by techniques well known in the art, such as for example, settling, coalescing, etc.

In commercial isobutane-olefin alkylation processes, an alkylation reaction effluent mixture is separated into a catalyst phase and a hydrocarbon phase by liquid-liquid separation means. The hydrocarbon phase comprises alkylated hydrocarbons, isobutane, and undesirable materials including ethane, propane, and normal butane which have entered the process mainly as components of the olefin and isobutane charge streams. As isobutane is used in the alkylation reaction in substantial molar excess, it is common practice to treat the hydrocarbon effluent from an alkylation reaction in a plurality of fractionation zones to separate a stream comprising isobutane which is recycled within the process to the alkylation reaction zone.

A major portion of the catalyst phase separated from an alkylation reaction effluent is commonly recycled to the alkylation reaction zone for use in alkylating additional amounts of isobutane with olefin. An alkylation catalyst containing sulfuric acid gradually loses its catalytic activity as it is recycled within an alkylation process. Accumulation of water, sulfonated polymeric hydrocarbons and other side reaction products within the catalyst phase serve to reduce the catalytic activity of the sulfuric acid. Consequently, a minor portion of the separated catalyst phase is withdrawn from the alkylation process as spent catalyst to remove by-products from the process. Fresh, make-up catalyst is added to the alkylation reaction zone to replace the amount of catalyst removed from the process as spent catalyst and to restore catalytic activity to the catalyst phase maintained in the alkylation reaction zone.

Many isobutane streams commonly available as charge stock for an alkylation process contain impurities in addition to such inert impurities as propane and normal butane. Impurities such as water, methylpropene, butadiene-1,3-propadiene, butyne-1, sulfur dioxide, hydrogen sulfide and methyl mercaptan are often found in isobutane streams available from petroleum refining processes. Such impurities as these react with sulfuric acid. The reaction of such impurities with sulfuric acid reduces the catalytic activity, or in some cases, such as the sulfur compounds, may destroy the catalytic effectiveness of sulfuric acid for alkylation of isobutane with olefins. Therefore, it is common practice to treat isobutane charge streams to remove such impurities prior to admitting such isobutane streams into the alkylation process. Treating methods such as caustic washing, adsorbing impurities upon adsorbents such as molecular sieves, silica-gel, etc. are well known in the prior art.

Water may be present in the isobutane as obtained from an outside source or may result from a treating step, such as caustic washing, employed to remove other reactive impurities from the isobutane. Treatment of isobutane with water adsorbers such as silica-gel, bauxite, molecular sieves, etc. is well known in the art. In such treating methods as described above for removing reactive impurities including water from the isobutane, the medium employed to treat the isobutane gradually losses its capacity for removing such impurities. Consequently, where treating methods such as caustic washing are employed, the caustic must be discarded and replaced with fresh caustic. Where treatment of isobutane with a solid adsorbent is employed, the adsorbent may be discarded or, in some events, regenerated.

SUMMARY OF THE INVENTION

Now according to the method of the present invention, an improved method is disclosed for treating an isobutane charge stream for removal of impurities which are reactive with sulfuric acid prior to charging such isobutane to an alkylation process catalyzed with a sulfuric acid containing catalyst. Such improved process comprises contacting isobutane, in the liquid phase, with spent sulfuric acid containing catalyst phase from an alkylation process for a time and under conditions sufficient to allow reaction of substantially all reactive impurities with sulfuric acid; separating a liquid isobutane stream substantially free of reactive impurities from the contacting step; charging such separated isobutane stream to an alkylation process; and removing from the contacting step a sulfuric acid phase comprising spent catalyst and reaction products of sulfuric acid and reactive impurities contained in the isobutane charge stream.

Operative conditions of the contacting step include spent catalyst-isobutane contact time of from about 0.1 to about 30 minutes, operating temperatures of from about 30°–200° F., and operating pressures of from about 45–400 psig, sufficient to maintain materials present in the contacting zone in the liquid phase. Preferably, the isobutane and spent catalyst are intimately contacted by such means as agitation, to ensure complete reaction of impurities with sulfuric acid. Spent sulfuric acid containing catalyst and liquid isobutane, upon agitation in the contacting zone, may form an emulsion. Such emulsion may be separated into a liquid isobutane phase and a sulfuric acid phase by such liquid-liquid separation means as gravity settling, coalescing, etc.

Under such conditions as described above, sulfuric acid from the spent catalyst will react with such impurities as water, dienes, acetylenes, sulfur compounds, and other reactive compounds to form reaction products which are soluble in the sulfuric acid phase and substantially insoluble in the liquid isobutane phase. By employing the method of this invention, isobutane treating methods such as caustic washing may be eliminated with the concomitant elimination of spent caustic disposal. Additionally an isobutane dryer for removal of water may be eliminated. With elimination of the dryer the necessity of regenerating adsorbent employed in such dryer is likewise eliminated. These and other advantages will be more fully described in the detailed description of the invention which follows.

BRIEF DESCRIPTION OF THE DRAWING

The drawing is a schematic representation of an olefin alkylation process showing an embodiment of the present invention.

DETAILED DESCRIPTION OF THE INVENTION

Alkylation of isobutane with butylenes and/or propylene in the presence of a sulfuric acid containing alkylation catalyst is well known. Such alkylation reactions are carried out in the liquid phase at temperatures of from about −20° F. to about 100° F., pressures of from about 45 psia to about 400 psia, residence times of from about 30 seconds to about 60 minutes, and with molar ratios of isobutane to olefin of from about 2:1 to about 25:1.

The sulfuric acid alkylation catalyst may be added to the alkylation reaction as sulfuric acid of about 90–98 wt. percent or as a mixture with other catalysts (such as fluorosulfonic acid) and/or catalyst promoters. When sulfuric acid is added to the alkylation reaction it reacts with olefins in the reaction mixture to form acid alkyl sulfates and dialkyl sulfates. These alkyl sulfates react with isobutane to form alkylate hydrocarbons. The preferred volume ratio of liquid hydrocarbon reactants to sulfuric acid containing alkylation catalyst in the alkylation reaction is in the range of from about 0.5:1 to about 3:1. The catalytic activity of sulfuric acid as a catalyst for alkylating isobutane with olefins may be substantially increased by using it in combination with other alkylation catalysts (eg. flurosulfonic acid) and/or employing catalyst promoters.

Sulfuric acid containing alkylation catalyst and liquid isobutane reactant are substantially immiscible, the alkylation reaction mixture is subjected to severe agitation or mixing such that an emulsion is formed, thereby insuring good contact of the hydrocarbon reactants with the catalyst. An alkylation reaction effluent comprising this hydrocarbon catalyst emulsion is separated by liquid-liquid separation means, such as gravity settling, centrifugation, coalescence, etc., into a hydrocarbon phase and a catalyst phase. The separated hydrocarbon phase of the alkylation reaction effluent comprises alkylated hydrocarbon, isobutane, unreacted olefin, and impurities including ethane, propane, normal butane, polymer hydrocarbon, and heavy alkylated hydrocarbons. The preferred alkylated hydrocarbons product from the alkylation reaction are highly branched hydrocarbons, such as trimethyl butanes, trimethyl pentanes, etc. which have unleaded Research Octane Numbers of about 100 and greater. Side reactions within the alkylation reaction produce less desirable hydrocarbon products including polymer hydrocarbons, heavy alkylate hydrocarbons and acid oils (sulfonated hydrocarbons). Such side reaction products have relatively low octane numbers and are undesirable components of motor fuels.

In a continuous process, the separated hydrocarbon phase is fractionated to recover alkylated hydrocarbon products, and isobutane for recycle. Also, the fractionation process removes impurities including, propane and butane from the alkylation process. Components of the catalyst phase such as acid oils and acid esters have an adverse effect upon fractionation equipment employed to fractionate the hydrocarbon phase. Such components of the catalyst phase, even in small amounts, lead to corrosion and plugging of fractionation process equipment. The separation process contemplated herein is sufficient for separating essentially all catalyst phase from the hydrocarbon phase of the alkylation reaction effluent. If necessary to ensure complete separation of the catalyst phase, intermediate treating of the separated hydrocarbon phase by such methods as bauxite treating is contemplated prior to fractionation.

It is economically desirable to recycle a major portion of the separated catalyst phase to the alkylation reaction to catalyze alkylation of additional hydrocarbon reactants while discarding, as spent catalyst, only a minor portion of the separated catalyst phase. Such spent catalyst is withdrawn to remove catalyst degradation products such as water, acid esters, and polymeric acid oils from the alkylation process. Hydrocarbon side reaction products are soluble in the alkylation cartalyst. Water dilutes the sulfuric acid of the catalyst, thus encouraging olefin polymerization side reactions at the expense of desired olefin-isobutane alkylation reactions. Consequently, in a continuous sulfuric acid catalyzed alkylation process wherein sulfuric acid containing alkylation catalyst is recycled for contact with additional hydrocarbon reactants, it is necessary to remove a portion of the catalyst as spent catalyst and replace that portion removed with fresh catalyst in order to maintain the desired catalytic activity.

According to the present invention, we have discovered that the amount of spent catalyst which must be removed from an alkylation process is sufficient to react with essentially all reactive impurities found in isobutane streams commonly employed as charge stock to such an alkylation process. The usefulness of such spent catalyst in treating an isobutane charge stream to a continuous alkylation process is demonstrated in the following example.

EXAMPLE 1

A sulfuric acid catalyzed alkylation process for alkylation of isobutane with butylene is operated to yield 5,000 barrels per day of alkylated hydrocarbon. In such process, isobutane and butylene, in a weight ratio of about 3:1 isobutane to butylene are contacted with an alkylation catalyst containing about 90 wt. percent sulfuric acid in a volume ratio of about 1:1 isobutane liquid to catalyst under conditions of severe agitation in an alkylation reaction zone. Agitation in the reaction zone is sufficient to maintain the isobutane phase-catalyst phase reaction mixture as an emulsion. Operating conditions within the alkylation reaction zone include reaction mixture residence time of about 30 minutes, a temperature of about 40° F., and a pressure of about 100 psig. Alkylation reaction zone effluent, comprising an emulsion, is separated by gravity settling into a hydrocarbon phase and a catalyst phase.

The separated hydrocarbon phase is fractionated to yield an alkylated hydrocarbon product fraction and an isobutane fraction. The unreacted isobutane is recovered for recycle to the alkylation reaction zone.

A major portion of the separated catalyst phase is recycled for contact with additional hydrocarbon reactants in the alkylation reaction zone. In order to maintain the catalytic activity of the catalyst, a small portion of the separated catalyst phase is removed from the process as spent catalyst and is replaced in the alkylation reaction zone with fresh 98 wt. percent sulfuric acid. A refinery isobutane stream of about 90 volume percent isobutane purity and containing 42 parts per million methylmercaptan and 185 parts per million water is charged to such alkylation process at a rate of 1,800 barrels per day. Another refinery stream comprising 40 volume percent butylenes and 20 volume percent isobutane is charged to the alkylation process at a rate of 7,350 barrels per day. Isobutane recycle, in an amount of 28,420 barrels per day, is circulated in the alkylation process.

In the process described above it is found that in order to maintain the catalytic activity of the sulfuric acid catalyst present in the alkylation reaction zone, it is necessary to add 12.6 pounds of 98 wt. percent sulfuric acid per 42 gallon barrel of $C_5^+$ alkylate produced. Spent alkylation catalyst is removed from the alkylation process in a volume amount sufficient to allow addition of fresh sulfuric acid and to maintain catalyst inventory relatively constant within the process. The amount of 90 percent sulfuric acid removed from the process in the spent catalyst when replaced at a rate of 12.6 pounds of 98 wt. percent sulfuric acid per 42 gallon barrel of alkylate is 68,600 pounds per day. This amount of sulfuric acid is far in excess of the amount (4,600 lbs/day) of sulfuric acid required to react with all the mercaptan and water entering the process via the isobutane charge stream.

In the example spent catalyst from the alkylation process and the make-up isobutane charge stream are charged to a contacting vessel wherein the isobutane and spent catalyst are contacted at a temperature of about 75° F., a pressure of about 250 psig, sufficient to maintain components in the liquid phase, with agitation to form an isobutane-spent catalyst emulsion, for a contact time of isobutane in the contacting vessel of about 5 minutes. Contacting vessel effluent is transferred to a settling vessel wherein a hydrocarbon phase comprising isobutane essentially free of water and methylmercaptan is separated from a spent catalyst phase containing substantially all the water and reaction products formed in the contacting vessel. A major portion of the separated spent catalyst phase from the settling vessel is returned to the contacting vessel to maintain a volume ratio of spent catalyst to isobutane of about 1:1. A minor portion of the spent catalyst phase from the settling vessel is removed in order to maintain inventory of spent catalyst phase as additional spent catalyst from the alkylation process is added to the contacting vessel. Such used spent catalyst phase from the settling vessel may be disposed of or may be regenerated to form sulfuric acid for use as catalyst in the alkylation process.

In order to better explain the process of the present invention, attention is now drawn to the attached drawings. Following is a description of one embodiment of the invention with reference to the drawing which is an alkylation process wherein an isobutane charge stream is contacted with spent catalyst in a contacting vessel and wherein treated isobutane is separated from spent catalyst in a separation vessel prior to charging to the alkylation process. The invention disclosed herein, the scope of which is defined in the appended claims, is not limited in its application to the details of the process and arrangement of parts shown and described in the drawing, since the invention is capable of other embodiments. Obvious variations and modifications of the present invention which are within the spirit and scope of the appended claims are considered to be incorporated herein.

In the drawing, an isobutane charge stream in line 10 containing reactive impurities such as water, methylmercaptans, dienes, and acetylenes and a recycle hydrocarbon fraction from line 19, as will hereinafter be described, are contacted in contacting zone 11 with spent catalyst from line 12, as will hereinafter be further described, under conditions of intimate mixing to form an isobutane-spent catalyst emulsion. Emulsion from contacting zone 11 passes via line 13 into separation zone 14 wherein an isobutane phase substantially free of reactive impurities is separated from a spent catalyst phase. Such separation is accomplished by gravity settling. A minor portion of separated spent catalyst is withdrawn and discarded from separation zone 14 via line 15 and a major portion of separated spent catalyst is returned via line 16 to contacting zone 11 to maintain therein the desired spent catalyst-isobutane ratio.

In the drawing, the treated isobutane stream which contains inert impurities such as propane and normal butane, is transferred from separation zone 14, via line 17 into depropanizing zone 18 which comprises a fractional distillation column. In depropanizing zone 18, treated isobutane stream is separated by fractionation into a $C_1$–$C_3$ fraction and a $C_4^+$ fraction. The $C_1$–$C_3$ fraction, comprising methane, ethane and propane from the fresh isobutane charge and from the recycle hydrocarbon stream is vented from depropanizing zone 18 via line 20. The $C_4$ stream comprising isobutane and normal butane is transferred from depropanizing zone 18 via line 21 to deisobutanizing zone 22. In deisobutanizing zone 22 the $C_4$ stream is separated by fractional distillation into an isobutane fraction and a normal butane and heavier fraction. The normal butane fraction is removed from deisobutanizing zone 22, and thus from the alkylation process, via line 23. Isobutane, substantially free of contaminants, is transferred from deisobutanizing zone 22, via line 24 to alkylation reaction zone 25. Olefin reactant, eg. butylenes and/or propylene, from line 26 is also charged to alkylation reaction zone 25. Recycle hydrocarbon, from line 27 (as will hereinafter be further described) comprising recycle isobutane, may also be charged to alkylation reaction zone 25. Alkylation catalyst from line 30 (as will hereinafter be further described), comprising recycle alkylation catalyst and fresh sulfuric acid is the final charge to alkylation reaction zone 25. In alkylation reaction zone 25, olefin and isobutane reactants in the liquid phase are agitated with sulfuric acid alkylation catalyst to form a reaction mixture emulsion, wherein isobutane is alkylated with olefin to produced alkylated hydrocarbons.

In the drawing, alkylation reaction emulsion from alkylation reaction zone 25 is transferred via line 28 to separation zone 29. In separation zone 29 the reaction emulsion effluent is separated by gravity settling into a hydrocarbon phase and a sulfuric acid catalyst phase. The separated catalyst phase is recycled from separation zone 29 via line 30 to alkylation zone 25 at a rate sufficient to maintain a selected level of separated catalyst phase in product separation zone 29. Spent alkylation catalyst from the alkylation process is removed from line 30 via line 12, in an amount such that the volume of catalyst phase does not increase upon addition of fresh sulfuric acid from line 26 into the alkylation process. From line 12, the spent alkylation catalyst passes into contacting zone 11 for contact with isobutane charge according to the improved method of the present invention hereinabove described.

In the drawing, separated hydrocarbon phase from product separation zone 29, comprising isobutane, alkylated hydrocarbons, diluents, including methane, ethane, propane, and normal butane, and alkylation reaction by products passes via line 31 into debutanizing zone 32. In debutanizing zone 32, said separated hydrocarbon phase is fractionated into a $C_5^+$ alkylate fraction and a recycle hydrocarbon fraction. The $C_5^+$ alkylate fraction, substantially free of normal butane and lighter hydrocarbons which increase the vapor pressure above a desired value, is recovered from debutanizing zone 32 via line 34 for use as a motor fuel blending component. Recycle hydrocarbon fraction is recovered from debutanizing zone 32 via line 33. Such recycle hydrocarbon fraction comprises primarily isobutane, along with diluents such as methane, ethane, propane and normal butane. Additionally, such recycle hydrocarbon may contain a small amount of water. A portion of recycle hydrocarbon fraction may be transferred from line 33 through line 27 as a charge stream to alkylation reaction zone 25, as hereinabove described. Preferably a portion, or all of said recycle hydrocarbon fraction is transferred from line 33 via line 19 to contacting zone 11, as hereinabove described. The portion of recycle hydrocarbon transferred via line 19 is selected such that water, excessive amounts of $C_1$–$C_3$ diluents and normal butane are removed from the alkylation process by treatment successively in contacting zone 11, depropanizing zone 18, and deisobutanizing zone 22 such that these compounds do not accumulate within the alkylation process to such an extent that they interfere with the alkylation reaction.

By following the process described above, isobutane charge and recycle hydrocarbon, containing reactive impurities such as water, mercaptans, dienes, and acetylenes, and inert diluents such as $C_1$–$C_4$ normal paraffins may be treated with spent sulfuric acid alkylation catalyst to remove reactive compounds therefrom and subsequently fractionated to remove inert diluents. The thus treated hydrocarbon stream, comprising mainly isobutane, may be charged to an alkylation process the efficiency of which is improved by the absence of such reactive compounds and inert diluents.

From the embodiments of the invention as shown in the drawing and set-out in the description above, modifications and variations of the present invention will occur to those skilled in the art, which modifications and variations are within the spirit and scope of the present invention. Therefore, it is intended that the present invention include all such modifications and variations, and that the only limitations contemplated are those contained within the appended claims.

We claim:

1. In a sulfuric acid catalyzed alkylation process wherein isobutane is contacted in an alkylation zone with propylene and/or butylene in the liquid phase, in the presence of a sulfuric acid containing alkylation catalyst, under alkylation conditions, and with agitation sufficient to form an emulsion of reactant hydrocarbons and catalyst, wherein propylene and/or butylene charge to said process contains $C_3$–$C_4$ range normal paraffin diluent hydrocarbons, wherein fresh isobutane charge to said process contains $C_3$–$C_4$ range normal paraffin diluents, and impurities reactive with sulfuric acid; the improvement which comprises:

(a) reacting, in an alkylation reaction zone, an isobutane stream substantially free of normal paraffin hydrocarbon and impurities which are reactive with sulfuric acid with an olefin stream comprising propylene and/or butylenes and containing $C_3$–$C_4$ normal paraffin diluents in the presence of a sulfuric acid alkylation catalyst for production of alkylated hydrocarbons;

(b) separating in a product separation zone, the reaction effluent from said alkylation reaction zone into a hydrocarbon phase essentially free of sulfuric acid catalyst and into a catalyst phase;

(c) recycling a major portion of said catalyst phase from said product separation zone to said alkylation reaction zone for said reacting step (a);

(d) fractionating, in a debutanizing zone, said separated hydrocarbon phase into a $C_5$ and heavier alkylated hydrocarbon product fraction and a recycle hydrocarbon fraction comprising isobutane with minor amounts of normal paraffin hydrocarbons and water;

(e) contacting, in a contacting zone, a minor portion of said catalyst phase from said product separation zone with a fresh isobutane charge stream containing $C_3$–$C_4$ normal paraffin diluents, water and impurities reactive with sulfuric acid and with said recycle hydrocarbon fraction from step (d) for conversion of said reactive impurities into compounds soluble in said catalyst phase and for absorption of water into said catalyst phase;

(f) separating, in a separation zone, the effluent from said contacting zone into a catalyst phase containing conversion products of said reactive impurities and absorbed water and into an isobutane phase containing normal paraffin impurities and substantially free of said reactive impurities and water;

(g) fractionating, in a depropanizing zone, said separated isobutane phase into a $C_1$–$C_3$ normal paraffin fraction and a depropanizing bottoms fraction comprising isobutane and n-butane;

(h) fractionating, in a deisobutanizing zone, said depropanizing zone bottoms fraction into a butane fraction comprising normal butane and any heavier hydrocarbons, and into an isobutane stream substantially free of normal paraffins, water, and reactive impurities; and (i) charging said isobutane stream from said deisobutanizing zone to said alkylation reaction zone as the isobutane stream of step (a).

2. The method of claim 1 wherein said fresh isobutane charge, said recycle hydrocarbon fraction, and said sulfuric acid catalyst phase are contacted in said contacting zone in the liquid phase at a temperature in the range of about 30° to about 200° F. for a period of from about 0.1 to about 30 minutes with agitation sufficient to form an emulsion and isobutane and catalyst for conversion of substantially all reactive impurities and for absorption of substantially all water into said catalyst phase.

3. The method of claim 2 wherein fresh sulfuric acid is added to said alkylation reaction zone for maintaining a preselected catalyst activity; wherein said minor portion of said catalyst phase passed from said product separation zone to said contact zone is in a volume sufficient to maintain a desired inventory of alkylation catalyst in said alkylation reaction zone; and wherein a portion of catalyst phase from separation zone is recycled with said minor portion of catalyst phase from said product separation zone to maintain a volume ratio of isobutane to catalyst phase of from about 1:1 to about 2:1 in said contacting zone.

* * * * *